United States Patent
Suzuki et al.

(10) Patent No.: US 8,158,365 B2
(45) Date of Patent: Apr. 17, 2012

(54) ANTI-2-O-DESULFATED ACHARAN SULFATE ANTIBODY AND ITS APPLICATION

(75) Inventors: Kiyoshi Suzuki, Higashiyamato (JP);
Takeshi Ishimaru, Higashiyamato (JP);
Koji Yamamoto, Higashiyamato (JP);
Yeong Shik Kim, Seoul (KR)

(73) Assignee: Seikagaku Corporation, Chiyoda-ku, Tokyo (JP)

( * ) Notice: Subject to any disclaimer, the term of this patent is extended or adjusted under 35 U.S.C. 154(b) by 640 days.

(21) Appl. No.: 12/297,047

(22) PCT Filed: Apr. 27, 2007

(86) PCT No.: PCT/JP2007/059556
§ 371 (c)(1),
(2), (4) Date: Nov. 28, 2008

(87) PCT Pub. No.: WO2007/126155
PCT Pub. Date: Nov. 8, 2007

(65) Prior Publication Data
US 2009/0280502 A1   Nov. 12, 2009

(30) Foreign Application Priority Data

Apr. 28, 2006   (JP) ................. 2006-127046

(51) Int. Cl.
*G01N 33/53* (2006.01)
*C07K 16/18* (2006.01)
*C07K 16/44* (2006.01)
*C12P 21/08* (2006.01)

(52) U.S. Cl. ............ 435/7.1; 530/388.1; 435/70.21; 422/430

(58) Field of Classification Search .............. None
See application file for complete search history.

(56) References Cited

U.S. PATENT DOCUMENTS

| | | | | |
|---|---|---|---|---|
| 4,208,479 A | * | 6/1980 | Zuk et al. | 435/7.9 |
| 5,696,100 A | * | 12/1997 | Holme et al. | 514/56 |
| 7,915,389 B2 | * | 3/2011 | Suzuki et al. | 530/388.1 |

OTHER PUBLICATIONS van de Westerlo et al. "Human single chain antibodies against heparin: selection, characterization, and effect on coagulation" Blood 2002 99: 2427-2433.*

Kim et al. "Determination of the structure of oligosaccharides prepared from acharan sulfate" Glycobiology vol. 8 No. 9 pp. 869-877, 1998.*

Joo et al. "Nucleolin: acharan sulfate-binding protein on the surface of cancer cells" Glycobiology vol. 15 No. 1 pp. 1-9, 2005.*

Suzuki et al. "Glycosaminoglycan chains of proteoglycans: approaches to the study of their structure and function" Pure Appl. Chem., 1991, vol. 63, No. 4, pp. 545-554.*

Harlow, E. and Lane, D., Antibodies: A Laboratory Manual (1988) Cold Spring Harbor Laboratory Press, Cold Spring Harbor, NY, pp. 7 and 139-142.*

Ishihara, et al. "Importance of 2-O-Sulfate Groups of Uronate Residues in Heparin for Activation of FGF-1 and FGF-2," *Journal of Biochemistry*, vol. 121, No. 2, pp. 345-349, Feb. 1997.

Kim, et al. "Purification and Characterization of Heparin Lyase I from *Bacteroides stercoris* HJ-15," *Journal of Biochemistry and Molecular Biology*, vol. 37, No. 6, pp. 684-690, Nov. 30, 2004.

Kim, et al. "A New Glycosaminoglycan from the Giant African Snail *Achatina fluica*," *The Journal of Biological Chemistry*, vol. 271, No. 20, pp. 11750-11755, May 17, 1996.

ten Dam, et al. "Detection of 2-O-Sulfated Iduronate and N-Acetylglucosamine Units in Heparan Sulfate by an Antibody Selected Against Acharan Sulfate (IdoA2S-GlcNAc)$_n$," *The Journal of Biological Chemistry*, vol. 279, No. 37, pp. 38346-38352, Sep. 10, 2004.

International Search Report dated Jul. 13, 2007.

* cited by examiner

*Primary Examiner* — Mark Shibuya
*Assistant Examiner* — Christine Foster
(74) *Attorney, Agent, or Firm* — Knobbe, Martens, Olson & Bear, LLP (57) ABSTRACT

An antibody that reacts with 2-O-desulfated acharan sulfate, a hybridoma that produces the antibody, a detection method and a detection kit to which the antibody is applied are disclosed. The antibody that reacts with 2-O-desulfated acharan sulfate can be produced by immunizing a mammal using as an antigen a substance obtained by chemically bonding a protein to 2-O-desulfated acharan sulfate.

6 Claims, 3 Drawing Sheets

ANTI-2-O-DESULFATED ACHARAN SULFATE ANTIBODY AND ITS APPLICATION

CROSS-REFERENCE TO RELATED APPLICATIONS

This application is the U.S. National Phase under 35 U.S.C. §371 of International Application PCT/JP2007/059556, filed Apr. 27, 2007, which claims priority to JP 2006-127046, filed Apr. 28, 2006.

TECHNICAL FIELD

The present invention relates to an anti-2-O-desulfated acharan sulfate antibody and its application.

BACKGROUND ART

The abbreviations used in this application are as follows:
AS: acharan sulfate,
ACH: 2-O-desulfated AS,
GAG: glycosaminoglycan,
HA: hyaluronic acid,
CS: chondroitin sulfate,
NAH: N-acetylheparosan,
HEP: heparin,
HS: heparan sulfate,
EHS-HS: HS derived from murine Engelbreth-Holm-Swarm sarcoma,
$NH_2$-HEP: N-desulfated HEP,
NAc-HEP: N-desulfated/N-re-acetylated HEP,
6DSH: 6-O-desulfated HEP,
NAc-6DSH: N-acetylated 6DSH,
$NH_2$-6SH: (2-O/N)-desulfated HEP,
6SH: (2-O/N)-desulfated/N-re-acetylated HEP,
$NH_2$-2SH: (6-O/N)-desulfated HEP,
2SH: (6-O/N)-desulfated/N-re-acetylated HEP,
NSH: (2-O/6-O)-desulfated HEP,
$NH_2$-CDSH: completely desulfated HEP,
CDSH: completely desulfated/N-re-acetylated HEP,
Ch: chondroitin,
2DSH: 2-O-desulfated HEP,
NAC-NSH; N-acetylated NSH,
CS-A(W): whale-derived chondroitin sulfate A,
CS-A(S): shark-derived chondroitin sulfate A,
CS-B: chondroitin sulfate B,
CS-C: chondroitin sulfate C,
CS-D: chondroitin sulfate D,
CS-E: chondroitin sulfate E,
KLH: hemocyanin, and
BSA: bovine serum albumin.

AS is one type of GAG isolated from a giant east African land snail (scientific name: *Achatina fulica*). As a compound obtained by chemically desulfating AS, ACH is known (Non-patent document 1). As an antibody that reacts with AS, MW3G3 is known (Non-patent document 2). However, an antibody that reacts with ACH has not been known.

Non-patent document 1: M. Ishihara et al., Journal of Biochemistry, Vol. 121, No. 7, pp. 345-349, 1997

Non-patent document 2: Gerdy B. ten Dam et al., Journal of Biological Chemistry, Vol. 279, pp. 38346-38352, 2004

DISCLOSURE OF THE INVENTION

An object of the present invention is to provide an antibody that reacts with ACH, a hybridoma that produces the antibody, a detection method and a detection kit to which the antibody is applied.

The inventors of the present invention have made intensive studies in view of the above-mentioned object, and as a result they found an antibody that reacts with ACH by using a substance obtained by chemically bonding a protein to ACH as an antigen, thus the present invention has been completed. That is, the present invention is as follows.

(1) An antibody which reacts with ACH (hereinafter referred to as an "antibody of the present invention").

(2) The antibody according to the above (1), which does not substantially react with AS.

(3) The antibody according to the above (1) or (2), which does not substantially react with NAH.

(4) The antibody according to any one of the above (1) to (3), which does not substantially react with HEP derived from porcine intestine.

(5) The antibody according to any one of the above (1) to (4), which does not substantially react with HS derived from bovine kidney.

(6) The antibody according to any one of the above (1) to (5), which does not substantially react with EHS-HS.

(7) The antibody according to any one of the above (1) to (6), which is a monoclonal antibody.

(8) The antibody according to the above (7), which is a monoclonal antibody produced by a hybridoma formed by cell fusion of a lymphocyte derived from a mammal immunized using as an antigen a substance obtained by chemically bonding a protein to ACH and a myeloma cell derived from a mammal.

(9) The antibody according to the above (8), wherein the lymphocyte and the myeloma cell are derived from a mouse.

(10) The antibody according to any one of the above (1) to (9) whose immunoglobulin class is IgM.

(11) A monoclonal antibody produced by a hybridoma deposited at Patent Organism Depositary, National Institute of Advanced Industrial Science and Technology under the deposit number of FERM BP-10779.

(12) A substance, which is obtained by chemically bonding a protein to ACH and has antigenicity capable of raising an antibody that reacts with ACH (hereinafter referred to as an "antigen of the present invention").

(13) A hybridoma formed by cell fusion of a lymphocyte derived from a mammal immunized using as an antigen a substance obtained by chemically bonding a protein to ACH and a myeloma cell derived from a mammal (hereinafter referred to as a "hybridoma of the present invention").

(14) The hybridoma according to the above (13), wherein the lymphocyte and the myeloma cell are derived from a mouse.

(15) A hybridoma deposited at Patent Organism Depositary, National Institute of Advanced Industrial Science and Technology under the deposit number of FERM BP-10779.

(16) A method for detecting ACH present in a sample, characterized by comprising at least a step of bringing an antibody according to any one of the above (1) to (11) into contact with the sample (hereinafter referred to as a "detection method of the present invention").

(17) The detection method according to the above (16), wherein the sample is derived from a material selected from the group consisting of a body fluid, a cell, a tissue, and a culture of a cell or a microorganism.

(18) A kit for detecting ACH present in a sample, comprising at least an antibody according to any one of the above (1) to (11) (hereinafter referred to as a "detection kit of the present invention").

(19) The detection kit according to the above (18), wherein the sample is derived from a material selected from the group consisting of a body fluid, a cell, a tissue, and a culture of a cell or a microorganism.

Because of the reactivity with ACH, the antibody of the present invention can be preferably used for detection of ACH. In addition, the antibody of the present invention can also be applied to ACH-specific detection. Further, by using the antigen of the present invention and the hybridoma of the present invention, the antibody of the present invention can be efficiently produced. Further, by the detection method of the present invention, ACH can be efficiently detected. Further, by using the detection kit of the present invention, detection of ACH by the detection method of the present invention can be performed more efficiently and conveniently.

BRIEF DESCRIPTION OF THE DRAWINGS

FIG. 3 is a graph showing the reactivity of ACH55 antibody against various types of HEP derivatives and the like.

DESCRIPTION OF THE PREFERRED EMBODIMENTS

<1> Antibody of the Present Invention

An antibody of the present invention is an antibody that reacts with ACH.

ACH is a polysaccharide having a repeating structure of the disaccharide unit composed of N-acetylglucosamine and iduronic acid (-[IdoA-GlcNAc]-) as a basic sugar chain structure. ACH can be prepared by preparing AS using a giant east African land snail (scientific name: *Achatina fulica*) as a raw material and desulfating the sulfate group on the 2-position of the iduronic acid residues in the resulting AS according to a known method. A more specific preparation method is described in Example 1 shown below.

In the above description, "reaction" means an immunological reaction or an antigen-antibody reaction, and the reactivity can be determined by an ELISA method, an RIA method, a plaque assay, an agglutination reaction method, a flow cytometry method, a histological staining method, a Western blotting method or the like. For example, when an ELISA method is performed using an antibody at a specified concentration, in the case where a reaction signal is increased in proportion to an increase in the concentration of an antigen, it can be said that the antibody reacts with the antigen. In this specification, unless otherwise specified, the reactivity of the antibody of the present invention against an antigen means a relative reactivity when the reactivity of the antibody of the present invention against ACH measured by a method described in Example 5 shown below (antigen concentration: 0.1 μg/well) is determined to be 100%.

The antibody of the present invention is not particularly limited as long as it is an antibody that reacts with ACH, however, preferable antibodies include an antibody that does not substantially react with AS, an antibody that does not substantially react with NAH, an antibody that does not substantially react with HEP derived from porcine intestine, an antibody that does not substantially react with HS derived from bovine kidney, and an antibody that does not substantially react with EHS-HS. Among these antibodies, an antibody that reacts with ACH and does not substantially react with any of AS, NAH, HEP derived from porcine intestine, HS derived from bovine kidney and EHS-HS is particularly preferred.

Further, it is preferred that the antibody of the present invention does not substantially react with one or more HEP derivatives selected from the group consisting of: $NH_2$-HEP, NAc-HEP, 6DSH, NAc-6DSH, $NH_2$-6SH, $NH_2$-2SH, NSH and $NH_2$-CDSH. In particular, it is more preferred that the antibody does not substantially react with any of the above-mentioned HEP derivatives.

The phrase "does not substantially react" as used herein means that the degree of reactivity between an antibody and an antigen is a degree to which a reaction signal is not given when measurement is performed by a method described in the Example 5 shown below (antigen concentration: 0.1 μg/well), however, in this specification, it shall also be construed to be a degree to which a reaction signal is not given when the degree of reactivity is, for example, about 5% or lower as compared with the reactivity against ACH.

Further, it is preferred that the antibody of the present invention reacts with CDSH.

The above-mentioned various types of GAG and various types of HEP derivatives are available or can be prepared by a method described in the Examples shown below.

An epitope of the antibody of the present invention is not particularly limited as long as it is a portion of ACH, however, it is preferably composed of an iduronic acid unit (-[IdoA-GlcNAc]-).

The antibody of the present invention may be either a monoclonal antibody or a polyclonal antibody, however, it is more preferably a monoclonal antibody. Further, the monoclonal antibody may be a fragment thereof. Examples of the fragment of the monoclonal antibody include F(ab')$_2$ antibodies, Fab antibodies, single chain antibodies (scFv), diabodies, minibodies and the like.

In the case where the antibody of the present invention is a monoclonal antibody, the antibody of the present invention can be produced, for example, by a hybridoma formed by cell fusion of a lymphocyte derived from a mammal immunized using as an antigen a substance obtained by chemically bonding a protein to ACH and a myeloma cell derived from a mammal.

Further, in the case where the antibody of the present invention is a polyclonal antibody, the antibody of the present invention can be obtained, for example, from the serum of a mammal immunized using as an antigen a substance obtained by chemically bonding a protein to ACH.

As the "protein" in the substance obtained by chemically bonding a protein to ACH, for example, BSA and KLH can be exemplified, and, in particular, KLH is preferred.

Further, as the method of chemically bonding a protein to ACH, a mode of the chemical bond is not particularly limited, however, a covalent bond is preferred, and a disulfide bond (hereinafter sometimes referred to as "—SS—") is more preferred. As the method of chemically bonding by a disulfide bond, for example, a method described below can be adopted. That is, ACH is reductive aminated and the resulting compound is reacted with 5 mM n-succinimidyl-3-(2-pyridyldithio)propionate (hereinafter referred to as "SPDP"), whereby 2-pyridyldithio propynylated ACH is obtained. This compound is reduced with a reducing agent such as dithiothreitol, whereby thiolated ACH is obtained. In the same manner, a protein is reacted with SPDP, whereby a 2-pyridyldithio propynylated protein is obtained. Then, by mixing a solution of the thiolated ACH and a solution of the 2-pyridyldithio propynylated protein, a. disulfide bond is formed between ACH and the protein, whereby an ACH-SS-protein is obtained.

An origin of the above-mentioned lymphocyte and myeloma cell is not particularly limited as long as they are derived from a mammal, and examples of the mammal include swine, cattle, mouse, rat and the like. In particular, mouse is preferred.

Further, in the above description, immunization can be carried out by subcutaneously injecting an antigen prepared by the above-mentioned method into a non-human mammal. The injection method is not limited to this, and it may be interperitoneal injection or intravenous injection. In general, immunization is performed several times, and, it is preferably performed by administration together with an adjuvant. As the adjuvant, those that can be expected to have an adjuvant effect such as alum, killed Mycobacterium tuberculosis, a nucleic acid, complete Freund's adjuvant or incomplete Freund's adjuvant may be used, and, Titer MAX Gold (manufactured by Sigma) is particularly preferred.

After the final immunization of a mouse is performed, the above-mentioned cell fusion can be carried out, for example, by a known method using a lymphocyte obtained from the lymph node or the spleen of the mouse and a cell of a tumor cell line such as a myeloma cell (generally, P3-NS-1/1-Ag4-1, P3-X63-Ag8-U1 (P3 U1), P3-X63-Ag8-653, SP2/0-Ag14 or the like derived from a BALB/c mouse).

Further, the above-mentioned hybridoma can be obtained, for example, by performing selection and cloning according to a method illustrated below. That is, a hybridoma that produces an antibody reacting with ACH is selected from supernatant of a cell culture in which hybridomas grow well by various analysis methods (such as an RIA method, a plaque assay, an agglutination reaction method, an ELISA method, a flow cytometry method, a histological staining method and a Western blotting method), and then, cloning is performed for the obtained hybridoma. As the cloning method, FACS (fluorescent activated cell sorter), a limiting dilution method or the like which is generally used may be employed. For example, it is preferred that the limiting dilution method is performed in such a manner that the number of cells per well on a 96-well plate is not more than 1. Whatever methods are used, it is preferred that cloning is performed twice repeatedly so as to obtain a single clone.

By culturing the thus obtained single clone by an in vitro culture method, an in vivo culture (ascitic fluid) method or the like, a monoclonal antibody can be produced. The antibody can be separated and purified from the obtained culture medium by appropriately combining general biochemical techniques such as salting out, ion exchange, gel filtration, affinity chromatography, electrophoresis and the like.

The immunoglobulin class of the antibody of the present invention is not particularly limited, however, it is preferably IgM.

As one example of the above-mentioned antibody of the present invention, a monoclonal antibody produced by a hybridoma deposited at Patent Organism Depositary, National Institute of Advanced Industrial Science and Technology under the deposit number of BP-10779 can be exemplified.

<2> Antigen of the Present Invention

The antigen of the present invention is a substance, which is obtained by chemically bonding a protein to ACH and has antigenicity capable of raising an antibody that reacts with ACH.

The explanation of the above-mentioned terms "protein" and "ACH" and the method of chemically bonding the protein to ACH is as described in the above section <1> "antibody of the present invention". In addition, the above-mentioned "reaction" means an immunological reaction or an antigen-antibody reaction in the same manner as described in the above section <1> "antibody of the present invention". The specific explanation is described in the above section <1> "antibody of the present invention".

In addition, whether or not the antigen has antigenicity capable of raising an antibody that reacts with ACH can be determined, for example, by immunizing a mammal using a substance obtained by chemically bonding a protein to ACH by the method described in the above section <1> "antibody of the present invention" and confirming whether or not the antibody is present in a sample derived from the immunized mammal by an RIA method, a plaque assay, an agglutination reaction method, an ELISA method, a flow cytometry method, a histological staining method, a Western blotting method or the like.

The above-mentioned antibody that reacts with ACH is preferably the antibody of the present invention. Therefore, the antigen of the present invention can be used for the purpose of producing the antibody of the present invention. In such a case, for example, as the antigen to be used for immunization described in the above section <1> "antibody of the present invention", the antigen of the present invention can be used. More specific explanation will be made in the Examples shown below.

<3> Hybridoma of the Present Invention

The hybridoma of the present invention is a hybridoma formed by cell fusion of a lymphocyte derived from a mammal immunized using as an antigen a substance obtained by chemically bonding a protein to ACH and a myeloma cell derived from a mammal.

The explanation of the above-mentioned terms "protein" and "ACH", the method of chemically bonding the protein to ACH, "immunization", "a lymphocyte derived from a mammal", "a myeloma cell derived from a mammal", "cell fusion" and "hybridoma" is as described in the above section <1> "antibody of the present invention".

As one example of the above-mentioned hybridoma of the present invention, a hybridoma deposited at Patent Organism Depositary, National Institute of Advanced Industrial Science and Technology under the deposit number of BP-10779 can be exemplified.

The hybridoma of the present invention can be used for the purpose of producing the antibody of the present invention (preferably, the antibody of the present invention which is a monoclonal antibody). Here, the antibody of the present invention can be produced, for example, by culturing the hybridoma of the present invention by an in vitro culture method, an in vivo culture (ascitic fluid) method or the like. More specific explanation will be made in the Examples shown below.

<4> Detection method of the Present Invention

The detection method of the present invention is a method for detecting ACH present in a sample, characterized by comprising at least a step of bringing the antibody of the present invention into contact with the sample.

The above-mentioned "sample" is not particularly limited as long as it contains or may contain ACH, however, the sample may be derived from a body fluid such as urine, blood, plasma, serum, synovial fluid or spinal fluid, a secreted substance, a cell such as an animal cell or a plant cell, a tissue, an organ, a culture of a cell or a microorganism (including, for example, a culture supernatant, etc.) or the like. The above-mentioned term "derived from" means that the sample may be a purified substance, an extracted substance or a specimen derived from any of the materials illustrated above, or may be as it is.

In the detection method of the present invention, as a specific method for detecting ACH present in a sample, in the case where a tissue specimen is used as a sample, a standard immunohistological staining method or the like can be used, and in the case where a body fluid, a culture supernatant or the like is used as a sample, an ELISA method, an RIA method, a sandwich assay, a competitive assay, a plaque assay, an agglutination reaction method, a flow cytometry method, a Western blotting method or the like can be used.

In the above-mentioned sandwich assay, for example, the antibody of the present invention may be attached to a solid phase such as a plate and used as a primary antibody, or the antibody of the present invention may be labeled and used as a secondary antibody.

According to the detection method of the present invention, based on the reactivity of the antibody of the present invention with ACH, ACH present in a sample can be efficiently detected. Further, the detection method of the present invention can be applied to ACH-specific detection by utilizing the specific reactivity of the antibody of the present invention against various types of antigens described in above section <1> "antibody of the present invention".

The detection in the detection method of the present invention may be either quantitative detection or qualitative detection. In the case of quantitative detection, the concentration of ACH present in a sample can be determined, for example, by preparing a calibration curve for a relationship between the ACH concentration and the detection results using ACH standard solutions whose ACH concentrations are known in advance and comparing a detection result for the sample in which the ACH concentration is not known to the calibration curve.

<5> Detection Kit of the Present Invention

The detection kit of the present invention is a kit for detecting ACH present in a sample, which contains at least the antibody of the present invention. With the use of the detection kit of the present invention, the detection method of the present invention can be carried out efficiently and conveniently. Examples of the "kit which contains at least the antibody of the present invention" as described in the above description include a kit containing the antibody of the present invention as it is (for example, a kit containing the antibody of the present invention dissolved in a solution, etc.), a kit containing a solid phase to which the antibody of the present invention has been attached, and a kit containing the antibody of the present invention labeled with an enzyme or the like. In addition, the above-mentioned term, "sample" means the same as described in the above section <4> "detection method of the present invention".

Further, the detection kit of the present invention may contain, in addition to the antibody of the present invention, a primary antibody, a secondary antibody, a reaction buffer, a washing solution, a reaction substrate, an ACH standard solution and the like.

EXAMPLES

Hereinafter, the present invention will be specifically described in more detail with reference to Examples.

Example 1

Reference Example 1

Preparation of AS and ACH

AS was prepared from a giant east African land snail (scientific name: *Achatina fulica*) according to the method of Kim, Y. S. et al. (J. Biol. Chem., 271, 11750 (1996)). By using the obtained AS as a raw material, ACH was prepared according to the method of Ishihara, M. et al. (J. Biochem., 121, 345 (1997)).

Reference Example 2

Preparation of 2-Pyridyl Disulfide Propionylated KLH

The introduction of a 2-pyridyl disulfide structure into KLH was carried out according to the method of Carlsson, J. et al. (Biochem. J., 173, 723 (1978)).

More specifically, 60 mg of KLH (manufactured by Sigma) was dissolved in 0.1 M phosphate buffer (pH 7.5)/0.1 M NaCl to make a final concentration of 2.5 mg/ml. To this solution, 5 mM N-succinimidyl-3-[2-pyridylthio]propionic acid (hereinafter referred to as "SPDP" (manufactured by Sigma)) dissolved in ethanol was added and mixed to make a final concentration of 0.238 mM, and the mixture was maintained at room temperature for 30 minutes. After being dialyzed against distilled water to remove excess SPDP, the mixed solution was lyophilized, whereby 59.4 mg of 2-pyridyl disulfide propionylated KLH (hereinafter referred to as "PDP-KLH") was obtained.

Reference Example 3

Preparation of ACH-BSA Conjugate Via Uronic Acid

Each of ACH and BSA (manufactured by Bayer) was separately dissolved in 0.1 M MES buffer (pH 5.5) to make a final concentration of 10 mg/ml to obtain an ACH solution and a BSA solution. The ACH solution (300 µl) and the BSA solution (150 µl) were mixed, and 400 µg of 1-(3-dimethylaminopropyl)-3-ethylcarbodiimide (hereinafter referred to as "EDC" (manufactured by PIERCE)) was added thereto, and then the mixture was maintained at room temperature for 20 hours with stirring. The resultant reaction solution was dialyzed overnight against distilled water and lyophilized, whereby 3.5 mg of ACH-BSA conjugate via uronic acid was obtained.

Reference Example 4

Preparation of Biotin-Labeled GAG and Biotin-Labeled HEP Derivatives

For HA derived from porcine skin (hereinafter simply referred to as "HA"), CS-A (W), CS-A(S), CS-B, CS-C, CS-D, CS-E, HS derived from bovine kidney (hereinafter simply referred to as "HS"), and KS derived from bovine cornea (hereinafter simply referred to as "KS"), those manufactured by Seikagaku Corporation were used. NAH was prepared from a culture of *E. coli* K5 according to the method described in JP-A-2004-18840. HEP derived from porcine intestine (hereinafter simply referred to as "HEP" in Examples) was purchased from Scientific Protein Laboratories. EHS-HS was prepared according to the method described in JP-B-7-53756.

Figure 1:
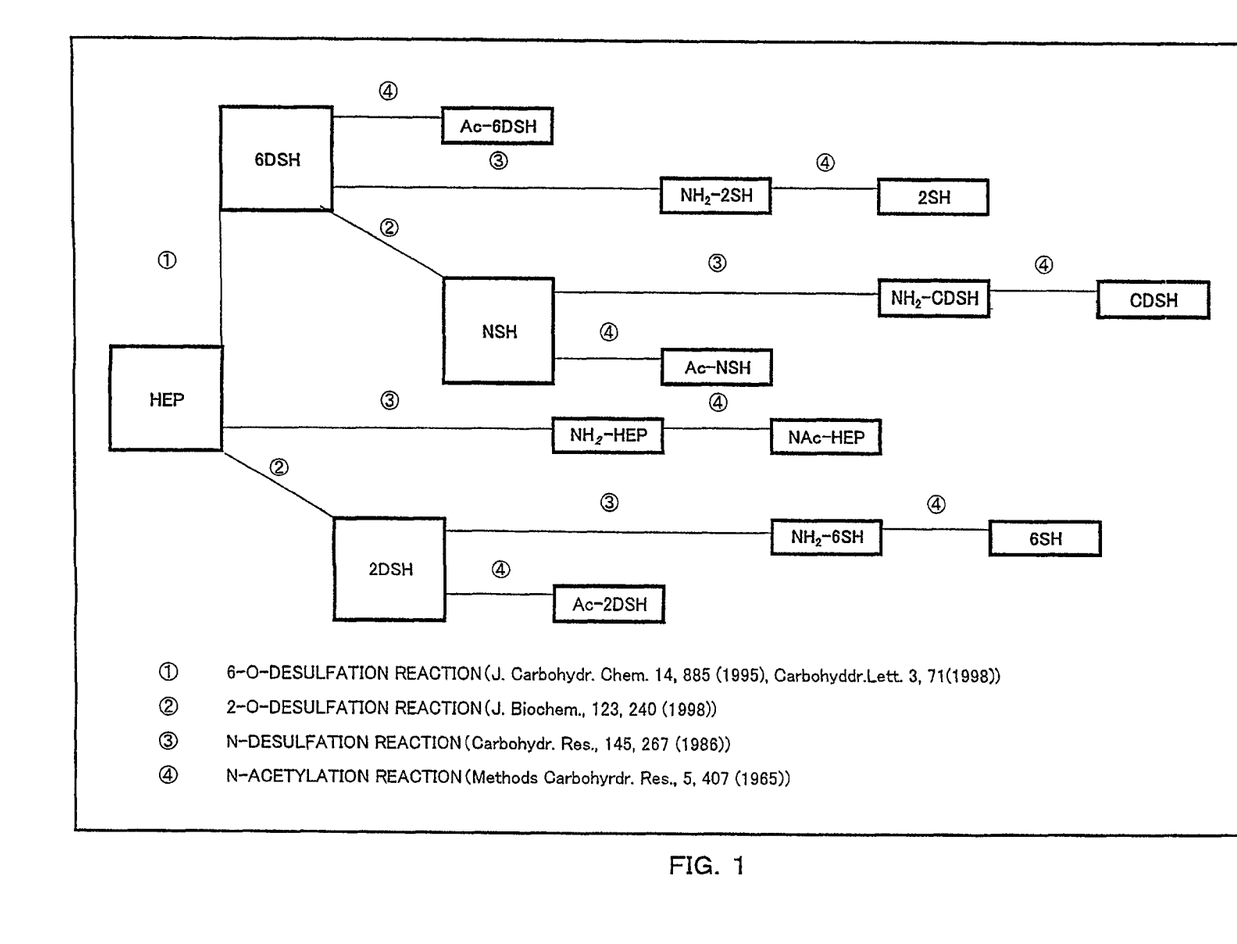
FIG. 1 is a view showing a flow of a method of producing various types of HEP derivatives.

Various types of HEP derivatives ($NH_2$-HEP, NAc-HEP, 6DSH, NAc-6DSH, $NH_2$-6SH, 6SH, $NH_2$-2SH, 2SH, NSH, NAc-NSH, $NH_2$-CDSH and CDSH) were prepared according to the method shown in FIG. 1. In FIG. 1, 6-O-, 2-O- and N-desulfation of HEP were carried out according to the methods of Takano et al., Kariya et al., and Ayotte, L. et al., respectively (Takano, R. et al., J. Carbohydr. Chem. 14, 885 (1995), Takano, R. et al., Carbohydr. Lett. 3, 71 (1998), Kariya, Y. et al., J. Biochem., 123, 240 (1998), and Ayotte, L. et al., Carbohydr. Res., 145, 267 (1986)).

N-acetylation was carried out according to the method of Danishefsky, I. et al. (Danishefsky, I. et al., Methods Carbohydr. Res., 5, 407 (1965)).

Because N-desulfation also occurs as a side reaction in some degree when 6-O-desulfation is carried out according to the method of Takano et al., part of the obtained 6DSH and NSH was subjected to N-acetylation to prepare NAc-6DSH and NAc-NSH.

Each of the above-mentioned various types of GAG and various types of HEP derivatives and AS and ACH prepared in Reference example 1 was separately dissolved in 0.1 M MES buffer (pH 5.5) to make a final concentration of 10 mg/ml and thereby, various types of GAG solutions and various types of HEP derivative solutions were obtained. To 1 ml of each of these various types of GAG solutions and various types of HEP derivative solutions, 25 μl of biotin-LC-hydrazide (manufactured by PIERCE) adjusted to be 20 mM with dimethylsulfoxide (manufactured by Wako Pure Chemical Industries) was added. Then, 12.5 μl of EDC solution adjusted to be 100 mg/ml with 0.1 M MES buffer (pH 5.5) was added thereto. After being mixed well, the mixed solution was allowed to react at room temperature (15° C. to 25° C.) for 20 hours with stirring. The resultant reaction product was subjected to dialysis using a dialysis membrane (cutoff; molecular weight 10,000 or smaller) against Dulbecco's phosphate buffered saline (pH 7.2 to 7.5, not containing divalent ions such as calcium ion, hereinafter referred to as "PBS(−)") to remove free biotin sufficiently, whereby various types of biotin-labeled GAG (hereinafter referred to as "Bi-GAG") and various types of biotin-labeled HEP derivatives (hereinafter referred to as "Bi-HEP derivatives") were obtained. After the dialysis, the concentration of Bi-GAG or Bi-HEP derivatives was adjusted to 5 mg/ml and cryopreserved.

Hereinafter, biotin-labeled ACH is referred to as "Bi-ACH".

Reference Example 5

Preparation of Streptavidin-Coated Microplate

Streptavidin (manufactured by Vector Laboratories) was diluted with PBS(−) to 20 μg/ml and 50 μl of this solution was added to each well of a Maxisor® (registered trademark; polystyrene based modified surface with a high affinity for polar groups) 96-well microplate (manufactured by Nunc). The plate was uniformly coated with streptavidin by storing it for 18 hours at 4° C., and then washed twice with PBS(−). Subsequently, by using AppliedDuo® (registered trademark, Soybean protein enzymatically hydrolyzed product, manufactured by Seikagaku Corporation) as a blocking agent, areas that were not coated with streptavidin were blocked according to the following method. That is, AppliedDuo® (registered trademark; Soybean protein enzymatically hydrolyzed product) (hereinafter referred to as a "blocking solution") was diluted by using a phosphate buffer containing 0.05% Proclin 300® (registered trademark, active ingredients in ProClin® are three isothiazolones, 2-Methyl-4-isothiazolin-3-one, 5-Chloro-2-methyl-4-isothiazolin-3-one and 1,2-Benzisothiazolin-3-one, manufactured by SUPELCO) as an antiseptic agent (pH 7.2 to 7.5, hereinafter referred to as "PB"), and 250 μl of this blocking solution was added to each well and the plate was let stand at room temperature for 2 hours. Thereafter, the blocking solution was removed sufficiently and the plate was dried at 37° C. for 2 hours, whereby a streptavidin-coated microplate was obtained. The obtained plate was enclosed in an aluminum-laminated bag with a desiccant and stored under refrigeration.

Reference Example 6

Preparation of Microplates Coated with Various Types of GAG and Microplates Coated with Various Types of HEP derivatives 1) Preparation of ACH-Coated Microplate The ACH-BSA conjugate (50 ng) prepared in Reference example 3 was added to a Maxisorp® (registered trademark; polystyrene based modified surface with a high affinity for polar groups) 96-well microplate and the plate was maintained for 18 hours at 4° C. Then, blocking was carried out using Block Ace® (registered trademark, blocking reagent, manufactured by, Dainippon Pharmaceutical Co., Ltd.) diluted 4-fold with PBS(−) containing 0.05% Proclin 300® (registered trademark active ingredients in ProClin® are three isothiazolones, 2-Methyl-4-isothiazolin-3-one, 5-Chloro-2-methyl-4-isothiazolin-3-one and 1,2-Benzisothiazolin-3-one) as an antiseptic agent. After the plate was let stand for 1 hour at room temperature, an ACH-coated microplate was obtained. This ACH-coated microplate was used to verify an antibody titer in the serum in the Example 3 shown below.

Each of various types of Bi-GAG and various types of Bi-HEP derivatives described in the above-mentioned Reference example 4 was separately dissolved in an AppliedDuo® (registered trademark; Soybean protein enzymatically hydrolyzed product) solution diluted 20-fold with PBS(−) containing 0.05% Proclin 300® (registered trademark; active ingredients in ProClin® are three isothiazolones, 2-Methyl-4-isothiazolin-3-one, 5-Chloro-2-methyl-4-isothiazolin-3-one and 1,2-Benzisothiazolin-3-one) to make a final concentration of 1 μg/ml (hereinafter these solutions are referred to as "various types of Bi-GAG solutions" and "various types of Bi-HEP derivative solutions"). Each well of the streptavidin-coated microplate prepared in Reference example 5 was washed 4 times with 300 μl of PBS(−) containing 0.05% Proclin 300® (registered trademark; active ingredients in ProClin® are three isothiazolones, 2-Methyl-4-isothiazolin-3-one, 5-Chloro-2-methyl-4-isothiazolin-3-one and 1,2-Benzisothiazolin-3-one) and 0.05% polyoxyethylene (20) sorbitan monolaurate (hereinafter referred to as a "washing buffer"). In each well, 100 μl of each of the various types of Bi-GAG solutions and various types of Bi-HEP derivative solutions was dispensed, and the plate was let stand for 30 minutes at room temperature. Then, each well was washed 4 times with the washing buffer, whereby microplates coated with various types of Bi-GAG and microplates coated with various types of Bi-HEP derivatives were obtained. These microplates were used for cloning in the Example 3 shown below and a reactivity test in the Example 5 shown below.

Example 2

Preparation of ACH Antigen

1) Preparation of Reductive Aminated ACH

Four point five milligrams of ACH prepared in Reference example 1 in Example 1 was weighed and dissolved in 160 µl of 2 M aqueous ammonium chloride solution. To this solution, 12 mg of sodium cyanohydridoborate was added and reductive amination reaction was carried out at 70° C. for 2 days. To the resultant reaction solution, 5 mg of sodium cyanohydridoborate was added and the reaction was carried out under the same conditions as described above for additional 2 days. The obtained solution was cooled in an ice bath and the reaction was completely terminated by adding 32 µl of acetic acid. By a solvent precipitation method using two volumes of ethanol, reductive aminated ACH (hereinafter referred to as "RA-ACH") was recovered. The obtained precipitate was washed with ethanol and then lyophilized, whereby 2.1 mg of lyophilized RA-ACH was obtained.

2) Preparation of 2-Pyridyl Disulfide Propionylated ACH

Two point one milligrams of RA-ACH prepared in the above 1) was dissolved in 1 ml of 0.1 M sodium chloride/0.1 M phosphate buffer (pH 7.5). After 80 µl of 5 mM SPDP ethanol solution was added to this solution, the mixture was let stand overnight at room temperature to allow a 2-pyridyl disulfide propionylation reaction (PDP reaction) to proceed. Dialysis was carried out using distilled water to remove excess SPDP, followed by lyophilization, whereby 1.7 mg of lyophilized 2-pyridyl disulfide propionylated ACH (hereinafter referred to as "PDP-ACH") was obtained.

3) Preparation of Thiopropionyl ACH

One point seven milligrams of PDP-ACH prepared in the above 2) was weighed and dissolved in 160 µl of 0.1 M sodium chloride/0.1 M sodium acetate buffer (pH 4.5). To this solution, dithiothreitol was added to make a final concentration of 25 mM and a reductive reaction was carried out for 60 minutes at room temperature. By a solvent precipitation method using two volumes of ethanol, thiopropionyl ACH (hereinafter referred to as "SH-ACH") was recovered. The obtained precipitate was washed with ethanol and then lyophilized, whereby 1.3 mg of lyophilized SH-ACH was obtained.

4) Preparation of ACH-KLH Conjugate Via Disulfide Bond

One point three milligrams of SH-ACH prepared in the above 3) and 0.65 mg of PDP-KLH prepared in Reference example 2 were dissolved in 1 ml of 0.1 M sodium chloride/ 0.1 M phosphate buffer (pH 7.5) and a conjugation reaction was carried out for 2 hours at room temperature. The resultant reaction solution was dialyzed overnight against distilled water to remove pyridyl-2-thione generated during the reaction, followed by lyophilization, whereby 1.5 mg of lyophilized ACH-KLH conjugate was obtained. The obtained lyophilized product was used as an ACH antigen in the following Example 3.

Example 3

Establishment of a Hybridoma Cell Line Producing an Antibody that Reacts with ACH 1) Immunization of a Mouse One milligram of the ACH antigen obtained in the above 4) in Example 2 was dissolved in a small amount of distilled water, and the solution was mixed with 2 ml of Titer MAX Gold® (registered trademark, TiterMax® contains three essential ingredients: A proprietary block copolymer CRL-8941, squalene, a metabolizable oil, and a unique microparticulate stabilizer, manufactured by Sigma), whereby an antigen solution was prepared. As animals for immunization, 4 BALB/C mice (6 weeks of age, female, produced by Charles River Japan, Inc.) were used. The above-mentioned antigen solution was subcutaneously administered every two weeks at 100 µl/animal for two or three times. When the antibody titer in the serum reached a sufficient level, 100 µl/animal of an ACH antigen solution without an adjuvant was administered as final immunization. Three days after the final immunization, the immunized mice were euthanized and the spleen was excised.

In the above description, the verification of the antibody titer in the serum was carried out according to the following method. That is, by using the ACH-coated microplate prepared in 1) in Reference example 6 and an alkaline phosphatase-labeled anti-mouse IgG+M+A (hereinafter referred to as "ALP anti-mouse Ig"), the antibody titer in the serum was verified by an enzyme-linked immunosorbent assay (ELISA). That is, 50 µl of the serum was dispensed in the ACH-coated microplate and the plate was incubated at 37° C. for 1 hour. Subsequently, the plate was washed 4 times with PBS(−), and then 50 µl of an ALP anti-mouse Ig solution diluted 1000-fold with 10% Block Ace® (registered trademark; blocking reagent)/PBS(−) was dispensed in each well. After the plate was washed 4 times with PBS(−), 50 µl of a substrate solution (ALP rose, manufactured by Shino-Test Corporation) was dispensed in each well and the plate was let stand for 20 minutes at room temperature. Then, 50 µl of a coloring reagent (manufactured by Shino-Test Corporation) was added thereto and an absorbance at 495 nm was measured using 660 nm as background correction.

2) Establishment of Hybridoma

Immunosensitized lymphocytes were collected from the spleen excised in 1) and mixed with mouse myeloma P3U1 cells (manufactured by SHIMA Laboratories Co., Ltd.) at a ratio of 4.4:1 to 5:1, and cell fusion was carried out by cocentrifugation in 50% polyethylene glycol 1500 (manufactured by Roche). As the myeloma cells to be used in the above cell fusion, the cells grown in an HAT medium containing 8-azaguanine for 1 week prior to the cell fusion were used. After the cell fusion, cells grown in the HAT medium were used in the following clone selection.

3) Selection and Evaluation of Clone 3-1) Cloning

A limiting dilution method was used for cloning. That is, cells were diluted with the HAT medium in such a manner that the number of cells per well was not more than 1, and dispensed into a 96-well microplate. The plate was incubated according to a standard method to obtain a culture supernatant. The evaluation of the antibody titer of the culture supernatant was carried out by an ELISA method using the Bi-ACH-coated microplate prepared in 2) in Reference example 6 and a clone having reactivity was selected. The above-mentioned cloning procedure was conducted at least twice. As a result, one clone was selected.

3-2) Evaluation of Clone

To confirm that the reactivity of the antibody produced from the clone obtained in the above 3-1) was maintained, the clone was cultured in a 24-well plate and the evaluation of the antibody titer of the obtained culture supernatant was carried out by an ELISA method using the Bi-ACH-coated microplate prepared in 2) in Reference example 6 and a horseradish peroxidase-labeled goat anti-mouse immunoglobulin (hereinafter referred to as "HRP anti-mouse Ig", manufactured by DAKO). The details are as follows.

[Evaluation of Antibody Titer of the Clone]

In the Bi-ACH-coated microplate washed 4 times with the washing buffer in advance, 100 μl of the culture supernatant was dispensed and the plate was let stand at room temperature for 1 hour. After the plate was further washed 4 times with the washing buffer, 100 μl of the HRP anti-mouse Ig, which was diluted 2000-fold with a reaction buffer (ApplieDuo® (registered trademark; Soybean protein enzymatically hydrolyzed product) solution diluted 20-fold with PBS(−) containing 0.05% Proclin 300® (registered trademark; active ingredients in ProClin® are three isothiazolones, 2-Methyl-4-isothiazolin-3-one, 5-Chloro-2-methyl-4-isothiazolin-3-one and 1,2-Benzisothiazolin-3-one), was dispensed in each well. After being let stand at room temperature for 1 hour, this plate was washed 4 times with the washing buffer and then, 100 μl of a tetramethyl benzidine solution (an HRP substrate solution, manufactured by BIOFX Laboratories, Inc.) was added to each well and an enzyme reaction was carried out for 30 minutes at 37° C. After the reaction, 100 μl of a coloring reagent (manufactured by BIOFX Laboratories, Inc.) was added to each well and an absorbance at 450 nm was measured using 630 nm as background correction. The reaction buffer was used as a negative blank. As a result, it was confirmed that the clone produces an anti-ACH antibody. Because the clone number of the established hybridoma was ACH55, the antibody produced by this hybridoma was named ACH55 antibody and this hybridoma was deposited at Patent Organism Depositary, National Institute of Advanced Industrial Science and Technology (AIST, Tsukuba Central 6, 1-1, Higashi 1-Chome, Tsukuba-shi, Ibaraki-ken, 305-8566, Japan) on Mar. 1, 2006 and the deposition number of FERM P-20828 was given. Then, it was converted into an international deposit under the Budapest Treaty and received an accession number FERM BP-10779. The immunoglobulin class of the antibody was examined according to a standard method, and as a result, the immunoglobulin class of ACH55 antibody was found to be IgM.

Example 4

Preparation of an Anti-ACH Monoclonal Antibody

1) Production of an Anti-ACH Monoclonal Antibody

As the method of producing an anti-ACH monoclonal antibody, a mouse ascitic fluid method was used. That is, $5 \times 10^6$ cells of the hybridoma (clone number: ACH55) established in the above 3) in Example 3 were injected into the abdominal cavity of a BALB/C mouse (15 weeks of age, female) which was treated with pristane (2,6,10,14-tetramethylpentadecane, Tokyo Chemical Industry Co., Ltd) in advance. During 10 to 20 days after the injection, the ascitic fluid of the mouse was collected several times separately and about 10 ml of ascitic fluid in total was obtained.

2) Purification of the Anti-ACH Monoclonal Antibody

The ascitic fluid obtained in the above 1) was dialyzed overnight against adsorption buffer 2 (20 mM phosphate buffer (pH 7.5) containing 0.5 M $K_2SO_4$). The dialysate was filtered with a membrane filter (pore size: 0.45 nm), and the obtained filtrate was applied to a HiTrap IgY Purification HP column (5 ml, manufactured by Amersham Biosciences) equilibrated with adsorption buffer 1 (20 mM phosphate buffer (pH 7.0)) in advance, and then the column was washed with the adsorption buffer 1. When the absorption at 280 nm of the washing solution passing through the column became almost 0, 20 mM phosphate buffer (pH 7.5) was applied to the column to elute ACH55 antibody. Then, by performing salting out using $(NH_4)_2SO_4$ (50% saturation), the eluted ACH55 antibody was recovered. The obtained precipitate was dialyzed against PBS(−) and thereby, the dialysate containing 2.2 mg of purified ACH 55 antibody was obtained.

Example 5

Reactivity Test

1) Reactivity of ACH55 antibody against various types of GAG

1)-1 Method

Bi-GAG-coated microplates were prepared in the same manner as in 2) in Reference example 6 except that the final concentration of Bi-GAG in a Bi-GAG solution used for coating was changed to 0.001, 0.004, 0.012, 0.037, 0.111, 0.333 or 1.000 μg/ml. The microplates were washed 4 times with the washing buffer, and then, 100 μl of each test solution, which contains ACH55 antibody diluted to be 0.06 μg/ml with PBS(−) containing ApplieDuo® (registered trademark, Soybean protein enzymatically hydrolyzed product, a final dilution of 20-fold, manufactured by Seikagaku Corporation) as an additive and 0.05% Proclin 300® (active ingredients in ProClin® are three isothiazolones, 2-Methyl-4-isothiazolin-3-one, 5-Chloro-2-methyl-4-isothiazolin-3-one and 1,2-Benzisothiazolin-3-one) as an antiseptic agent (hereinafter referred to as "reaction solution A"), was added to each well, and the plate was let stand at room temperature for 60 minutes to allow an antigen-antibody reaction to proceed. After the reaction, each well was washed 4 times with the washing buffer and then, 100 μl of a solution of a horseradish peroxidase-labeled goat anti-mouse immunoglobulin antibody (manufactured by Dako) obtained by diluting the antibody 2000-fold with the reaction solution A was added to each well as a secondary antibody solution and the plate was let stand at room temperature for 60 minutes to allow an antigen-antibody reaction to proceed. After the reaction, this plate was washed 4 times with the washing buffer and then, 100 μl of a tetramethyl benzidine solution (hereinafter referred to as "TMB solution", manufactured by BIOFX Laboratories, Inc.) as a substrate for peroxidase was added to each well, and the reaction was allowed to proceed at room temperature for 30 minutes for developing color. Then, 100 μl of a reaction termination solution (manufactured by BIOFX Laboratories, Inc.) was added to the plate for terminating the reaction, and an absorbance at a wavelength of 450 nm (a reference wavelength of 630 nm) that increases with TMB decomposition was measured with a Well Reader SK-603® (registered trademark, The Wellreader SK603 is (1→3)-β-D-glucan assay equipment that uses the Fungitec G test MK., distributed by Seikagaku Corporation). The reactivity of the antibody was evaluated based on an absorbance difference obtained by subtracting the absorbance in a well containing the reaction solution A (blank) as a test solution from the absorbance in a well containing the ACH55 antibody solution was used as a test solution (hereinafter referred to as an "absorbance difference").

1)-2 Results

Figure 2:
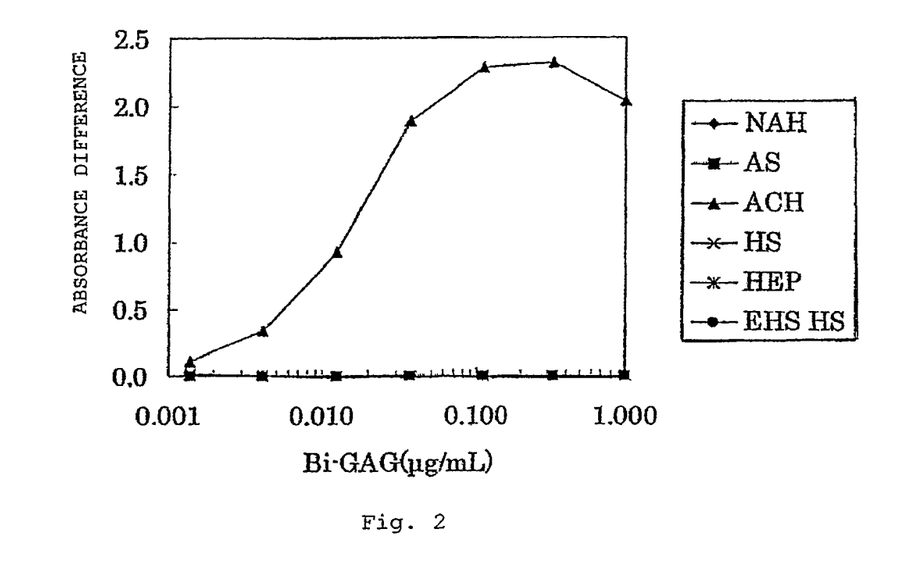
FIG. 2 is a graph showing the reactivity of ACH55 antibody against various types of GAG. Bi-GAG (μg/ml) on the horizontal axis indicates the final concentration of Bi-GAG in a Bi-GAG solution used for preparing a Bi-GAG-coated plate.

The results in the case where NAH, AS, ACH, HS, HEP and EHS-HS were used as GAG for Bi-GAG-coated microplates are shown in FIG. 2.

Although ACH55 antibody strongly reacted with ACH even when the concentration of each Bi-ACH was set to 0.01 μg/ml (0.001 μg/well) (absorbance difference=about 1.0), it did not react with AS, HEP, HS, NAH or EHS-HS even when the concentration of each Bi-GAG was raised to 1.0 µg/ml (0.1 µg/well) (FIG. 2).

Further, ACH55 antibody did not react with HA, various types of CS (CS-A(W), CS-A(S), CS-B, CS-C, CS-D and CS-E), or KS in the same manner as the case of HEP described above.

2) Reactivity of ACH55 Antibody Against Various Types of HEP Derivatives

The reactivity of ACH55 antibody against various types of HEP derivatives was evaluated. As the HEP derivatives for microplates coated with Bi-HEP derivatives, $NH_2$-HEP, NAc-HEP, 6DSH, NAc-6DSH, $NH_2$-6SH, 6SH, $NH_2$-2SH, 2SH, NSH, NAc-NSH, $NH_2$-CDSH and CDSH were used. In this test, the concentration of a solution containing any of the Bi-HEP derivatives used for coating was fixed at 1 µg/ml (0.1 µg/well). The results are shown in FIG. 3.

Figure 3:
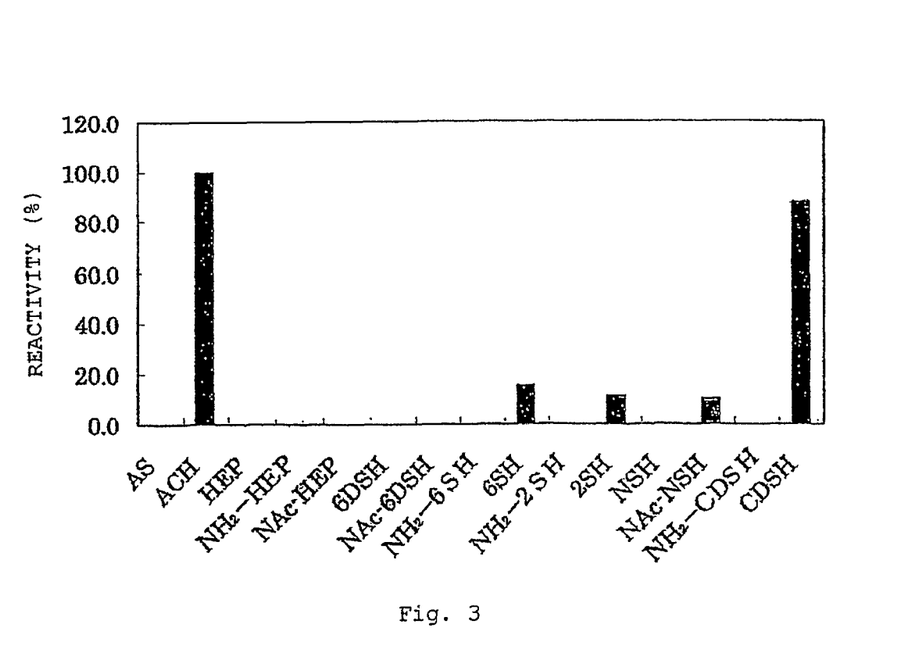

ACH55 antibody reacted strongly with CDSH, but reacted very weakly with 2SH, 6SH and NAc-NSH (FIG. 3).

Because ACH, with which ACH55 antibody reacted strongly, has an iduronic acid unit (-[IdoA-GlcNAc]-) as a major constituent disaccharide, the epitope of ACH55 antibody is considered to be composed of the iduronic acid unit. In addition, because NAH, with which the antibody did not react, is an uronic acid C5-epimer of ACH, which is composed of an N-acetylglucosamine unit (-[GlcA-GlcNAc]-), it was indicated that especially an iduronic acid residue is essential for ACH55 antibody to recognize an antigen. Further, because no reactivity is observed against AS (the hydroxyl group on the 2-position of the iduronic acid residue has been sulfated), it was indicated that the sulfation of iduronic acid residues (IdoA(2S)) inhibits the reactivity of ACH55 antibody against an antigen.

CDSH is a polysaccharide composed of an N-acetylglucosamine unit and an iduronic acid unit and the existing ratio of the iduronic acid unit is high (60% or more). Therefore, there is no discrepancy in the result that CDSH reacted with the antibody. In addition, because this reactivity was lost by N-deacetylation of CDSH ($NH_2$-CDSH) and N-sulfation (NSH) of a glucosamine residue in $NH_2$-CDSH (NSH), it was indicated that the acetylation of the amino group in a glucosamine residue is also important for ACH55 antibody to recognize an antigen.

Because it is known that a hexasaccharide containing iduronic acid (AUA(2S)-1,4-α-GlcNS(6S)-1,4-α-IdoA-1,4-α-GlcNAc(6S)-1,4-α-GlcA-1,4-α-GlcNS(3S) (6S)) is present in HEP at the ratio of 5 to 6% (Rice, K. G. and Linhardt, J. L., Carbohydr. Res., 190, 219-233 (1989)), it was inferred that the antibody that does not react with AS reacted weakly with 2SH, 6SH and NAc-NSH because of the exposure of the iduronic acid unit in an HEP derivative during various modifications such as N-, 2-O, and 6-O desulfation.

Example 6

Histological Staining

Immunohistological staining was performed using a frozen section of rat cerebellum.

An SD rat (produced by Charles River Japan, Inc., 8 weeks of age, male) was anesthetized with diethyl ether (manufactured by Wako Pure Chemical Industries) and killed by exsanguination via the abdominal aorta, and then the cerebellum was excised. The excised cerebellum was embedded into OCT compound (manufactured by Sankyo Miles) and frozen with acetone/dry ice and a section of 6 µm in thickness was prepared using a Cryostat (distributed by Leica).

After the prepared section was air-dried for 2 hours at room temperature, it was fixed using chilled acetone (4° C.) and further air-dried at room temperature for an additional 1 hour. Then, the section was washed with PBS(−) containing 0.1% BSA and soaked in distilled water containing 0.1% sodium azide (manufactured by Wako Pure Chemical Industries) and 0.3% hydrogen peroxide solution (manufactured by Wako Pure Chemical Industries) at room temperature for 10 minutes, whereby an endogenous peroxidase activity was quenched. Then, the section was washed with PBS(−) containing 0.1% BSA and then, blocking was carried out with PBS(−) containing 0.1% BSA and 0.1% casein (manufactured by Wako Pure Chemical Industries) at room temperature for 60 minutes.

Then, the section was washed with PBS(−) containing 0.1% BSA, and the blocking of endogenous biotin was carried out using an Avidin-biotin blocking kit (manufactured by VECTOR Laboratories).

Thereafter, the section was washed with PBS(−) containing 0.1% BSA, and then, ACH55 antibody diluted to 1 µg/ml with PBS(−) containing 0.1% BSA and 0.1% casein was reacted overnight at 4° C. After the section was washed with PBS(−) containing 0.1% BSA, biotin-labeled anti-mouse IgG+IgM (manufactured by JACKSON) containing 10% rat serum, which was diluted 500-fold with PBS(−) containing 0.1% BSA and 0.1% casein, was reacted at room temperature for 30 minutes. After the section was washed with PBS(−) containing 0.1% BSA, peroxidase-labeled streptavidin (manufactured by NICHIREI CORPORATION) was reacted at room temperature for 30 minutes. After the section was washed with PBS(−) containing 0.1% BSA, a brown color development reaction was carried out using a DAB color development kit (manufactured by ZYMED LABORATORIES).

After the color development, the reaction was terminated by soaking the section in PBS(−) containing 0.1% BSA, and the section was washed with water for 5 minutes. Thereafter, nuclear staining (blue) was carried out using hematoxylin (manufactured by DAKO) for contrast staining. After the section was washed with water for 5 minutes, dehydration and penetration treatment were carried out for embedding according to a standard method.

Figure 4:
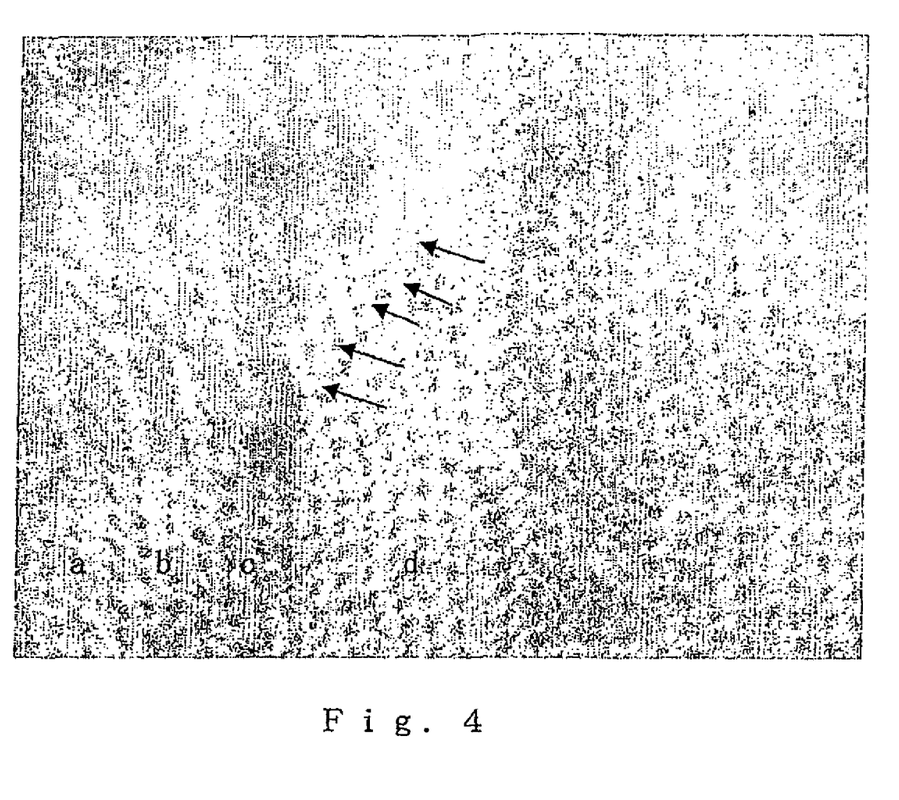
FIG. 4 is an image (photograph) showing the result of histological staining of rat cerebellum using ACH55 antibody. a: MOLECULAR LAYER, b: PURKINJE CELL LAYER, c: GRANULAR LAYER, d: WHITE MATTER

The obtained staining image is shown in FIG. 4. Positive signals were observed in the Purkinje cell (shown by arrows)

INDUSTRIAL APPLICABILITY

The antibody of the present invention is extremely useful because it can be preferably used for detecting ACH. In addition, the antigen of the present invention and the hybridoma of the present invention are very useful because they can be used for efficiently producing the antibody of the present invention. Further, according to the detection method of the present invention, ACH can be preferably detected, therefore, the method is extremely useful. Further, the detection kit of the present invention is very useful because by using this kit, the detection method of the present invention can be more efficiently and conveniently performed.

What is claimed is:

1. A monoclonal antibody produced by a hybridoma deposited at Patent Organism Depositary, National Institute of Advanced Industrial Science and Technology under the deposit number of FERM BP-10779.

2. A hybridoma deposited at Patent Organism Depositary, National Institute of Advanced Industrial Science and Technology under the deposit number of FERM BP-10779.

3. A method for detecting 2-O-desulfated acharan sulfate present in a sample, characterized by comprising at least a step of bringing the antibody of claim 1 into contact with the sample and detecting the presence of 2-O-desulfated acharan sulfate in the sample.

4. The method according to claim 3, wherein the sample is derived from a material selected from the group consisting of a body fluid, a cell, a tissue, and a culture of a cell or a microorganism.

5. A kit for detecting 2-O-desulfated acharan sulfate present in a sample, comprising at least the antibody of claim 1.

6. The kit according to claim 5, wherein the sample is derived from a material selected from the group consisting of a body fluid, a cell, a tissue and a culture of a cell or a microorganism.

* * * * *

UNITED STATES PATENT AND TRADEMARK OFFICE
CERTIFICATE OF CORRECTION

PATENT NO. : 8,158,365 B2
APPLICATION NO. : 12/297047
DATED : April 17, 2012
INVENTOR(S) : Suzuki et al.

It is certified that error appears in the above-identified patent and that said Letters Patent is hereby corrected as shown below:

First Page, Column 1, § 371 (c)(1), (2), (4) Date:, "November 28, 2008" should be changed to
--November 25, 2008--

First Page, Column 2, Line 23, "*Achatina fluica*,"" should be changed to --*Achatina fulica*,"--

Column 1, Line 42, "NAC-NSH;" should be changed to --NAc-NSH:--

Column 1, Line 53, "ACHis known" should be changed to --ACH is known--

Column 5, Line 4, "a. disulfide bond" should be changed to --a disulfide bond--

Column 5, Line 17, "interperitoneal injection" should be changed to --intraperitoneal injection--

Column 9, Line 60, "of a Maxisor®" should be changed to --of a Maxisorp®--

Column 10, Line 32, "manufactured by," should be changed to --manufactured by--

Column 10, Line 42, After "shown below." please insert the following:
--2) Preparation of microplates coated with various types of Bi-GAG and microplates coated with various types of Bi-HEP derivatives.--

Column 12, Line 28, "reagent)/PBS(-) was" should be changed to --reagent,)/PBS(-) was--

Column 14, Line 53, "G test MK.," should be changed to --G test MK,--

Column 16, Line 44, "(shown by arrows)" should be changed to --(shown by arrows).--

Signed and Sealed this
Ninth Day of October, 2012

David J. Kappos
*Director of the United States Patent and Trademark Office*